US 11,547,439 B2

(12) United States Patent
Williams

(10) Patent No.: US 11,547,439 B2
(45) Date of Patent: Jan. 10, 2023

(54) SURGICAL INSTRUMENTS INCLUDING DEVICES FOR SENSING TISSUE PROPERTIES AND METHODS THEREOF

(71) Applicant: Covidien LP, Mansfield, MA (US)

(72) Inventor: Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 1143 days.

(21) Appl. No.: 16/140,627

(22) Filed: Sep. 25, 2018

(65) Prior Publication Data
US 2019/0175215 A1 Jun. 13, 2019

Related U.S. Application Data

(60) Provisional application No. 62/597,595, filed on Dec. 12, 2017.

(51) Int. Cl.
A61B 17/11 (2006.01)
A61B 17/29 (2006.01)
(Continued)

(52) U.S. Cl.
CPC ............ *A61B 17/3421* (2013.01); *A61B 5/00* (2013.01); *A61B 5/0053* (2013.01); *A61B 5/01* (2013.01);
(Continued)

(58) Field of Classification Search
CPC ....... A61B 17/3421; A61B 34/30; A61B 5/00; A61B 5/0053; A61B 5/01; A61B 5/0538; A61B 5/6847; A61B 5/6885; A61B 17/11; A61B 17/2909; A61B 2090/065; A61B 5/1036; A61B 17/3462; A61B 2017/00022; A61B 2017/00026; A61B 2017/00084; A61B 2017/0011; A61B 2017/00221; A61B 2017/00367; A61B 2017/00398; A61B 2017/0046; A61B 2017/00477;
(Continued)

(56) References Cited

U.S. PATENT DOCUMENTS 6,517,565 B1 2/2003 Whitman et al.
2004/0254606 A1 12/2004 Wittenberger et al.
(Continued)

OTHER PUBLICATIONS

U.S. Appl. No. 16/140,664, filed Sep. 25, 2018.
(Continued)

*Primary Examiner* — Matthew Kremer
*Assistant Examiner* — Om Patel
(74) *Attorney, Agent, or Firm* — Carter, DeLuca & Farrell, LLP

(57) ABSTRACT

A sensing device for sensing one or more tissue properties includes an adapter assembly, an actuation assembly, a shuttle, and a piston assembly. The adapter assembly is configured to couple to surgical handheld devices. The actuation assembly extends distally from the adapter assembly and is configured to operably couple to and be engaged by handheld devices coupled thereto. The actuation assembly includes a first drive shaft and a second drive shaft. The shuttle has a clamp and a shuttle sensor, and is coupled to the first drive shaft via a coupling. The shuttle sensor is disposed on the clamp. The piston assembly is coupled to the second drive shaft and configured to compress target tissue between the piston assembly and the clamp of the shuttle.

20 Claims, 8 Drawing Sheets

(51) Int. Cl.
  *A61B 5/00*    (2006.01)
  *A61B 5/0538*  (2021.01)
  *A61B 5/01*    (2006.01)
  *A61B 90/00*   (2016.01)
  *A61B 17/34*   (2006.01)
  *A61B 34/30*   (2016.01)
  *A61B 5/103*   (2006.01)
  *A61B 17/00*   (2006.01)

(52) U.S. Cl.
  CPC .......... *A61B 5/0538* (2013.01); *A61B 5/6847* (2013.01); *A61B 5/6885* (2013.01); *A61B 17/11* (2013.01); *A61B 17/2909* (2013.01); *A61B 34/30* (2016.02); *A61B 5/1036* (2013.01); *A61B 17/3462* (2013.01); *A61B 2017/0011* (2013.01); *A61B 2017/00022* (2013.01); *A61B 2017/00026* (2013.01); *A61B 2017/0046* (2013.01); *A61B 2017/00084* (2013.01); *A61B 2017/00221* (2013.01); *A61B 2017/00367* (2013.01); *A61B 2017/00398* (2013.01); *A61B 2017/00477* (2013.01); *A61B 2017/2944* (2013.01); *A61B 2090/065* (2016.02); *A61B 2505/05* (2013.01); *A61B 2562/0209* (2013.01); *A61B 2562/0252* (2013.01); *A61B 2562/0261* (2013.01); *A61B 2562/0271* (2013.01)

(58) Field of Classification Search
  CPC ........ A61B 2017/2944; A61B 2505/05; A61B 2562/0209; A61B 2562/0252; A61B 2562/0261; A61B 2562/0271; A61B 5/683; A61B 5/6834; A61B 5/6835; A61B 5/6838; A61B 1/00137; A61B 2018/0225; A61B 17/122; A61B 17/1285; A61B 17/320092; A61B 2017/320094; A61B 5/6884

See application file for complete search history.

(56) References Cited

U.S. PATENT DOCUMENTS

| | | |
|---|---|---|
| 2008/0029577 A1* | 2/2008 | Shelton ................ A61B 17/072 227/176.1 |
| 2015/0157320 A1 | 6/2015 | Zergiebel et al. |
| 2016/0066914 A1* | 3/2016 | Baber ...................... H02H 1/06 227/176.1 |
| 2016/0296234 A1 | 10/2016 | Richard et al. |
| 2016/0310134 A1 | 10/2016 | Contini et al. |
| 2017/0273700 A1 | 9/2017 | Wakai et al. |
| 2018/0250002 A1 | 9/2018 | Eschbach |

OTHER PUBLICATIONS

U.S. Appl. No. 62/661,821, filed Apr. 24, 2018.
U.S. Appl. No. 62/661,242, filed Apr. 25, 2018.
Extended European Search Report corresponding to counterpart Patent Application EP 18211539.4 dated Apr. 18, 2019.

* cited by examiner

SURGICAL INSTRUMENTS INCLUDING DEVICES FOR SENSING TISSUE PROPERTIES AND METHODS THEREOF

CROSS-REFERENCE TO RELATED APPLICATION

This application claims the benefit of and priority to U.S. Provisional Patent Application No. 62/597,595 filed Dec. 12, 2017, the entire disclosure of which is incorporated by reference herein.

BACKGROUND

Technical Field

The present disclosure relates generally to surgical instruments used during minimally invasive surgical procedures and, more particularly, to systems and methods for measuring one or more tissue properties during a surgical procedure within a body cavity of a patient.

Related Art

During surgical procedures medical professionals or clinicians may find it desirable to determine one or more tissue properties prior to acting upon the tissue. For example, during colorectal surgeries which require anastomosis, the clinician visually inspects the tissue of the colon to be resected. Typically, during inspection, the clinician visually observes the colon and determines which portion or portions of the colon are diseased. The clinician then identifies which diseased portions of the colon will be removed. Observation may be performed via one or more imaging devices positioned within the colon or proximate to the colon. Various other surgical procedures require similar visual inspection of tissue to determine which portions of tissue are to be removed.

Depending on the procedure and the tissue being examined, the clinician may not identify all areas of concern due to the limited visibility of the clinician. For example, referring again to anastomotic procedures, the colon may include an abnormal growth which may not be easily visualized from an inspection of the exterior of the colon. As such, the clinician may need to inspect the interior of the tissue to be resected as well. Inspection of the interior of the colon may require additional clinicians to assist in imaging the interior of the colon. Additionally, care must be taken when aligning the interior and exterior views during the imaging process.

As such, improved devices and methods for evaluating tissue properties during a surgical procedure are desirable.

SUMMARY

Existing challenges associated with the foregoing, as well as other challenges, are overcome by methods for identifying one or more properties of target tissue, and also by systems and apparatuses that operate in accordance with these methods.

According to an example embodiment herein, a sensing device for sensing one or more tissue properties is disclosed. The sensing device includes an adapter assembly, an actuation assembly, a shuttle, and a piston assembly. The adapter assembly is configured to couple to surgical handheld devices. The actuation assembly extends distally from the adapter assembly. The actuation assembly is configured to operably couple to and be engaged by handheld devices coupled to the adapter assembly. The actuation assembly includes a first drive shaft and a second drive shaft. The shuttle has a clamp and a shuttle sensor. The shuttle is coupled to the first drive shaft via a coupling. The shuttle sensor is disposed on the clamp of the shuttle. The piston assembly is coupled to the second drive shaft and configured to compress target tissue between the piston assembly and the clamp of the shuttle.

In aspects, the shuttle sensor is configured to sense one or more tissue properties selected from the group consisting of tissue temperature, tissue impedance, tissue permittivity, tissue permeability, tissue elasticity, and force applied by the sensing device to target tissue.

According to aspects, the first drive shaft and the second drive shaft of the actuation assembly are rotatably supported and configured to receive rotational force from motors operably coupled thereto. Rotation of the first drive shaft may cause the shuttle to advance proximally to clamp target tissue. Rotation of the second drive shaft may cause the piston assembly to advance distally to compress target tissue.

In aspects, the sensing device further includes a trip sensor and a trip spring. The trip spring is coupled to the coupling and the shuttle. The trip spring may exert a tensile force to urge the coupling toward a proximal-most position relative to the shuttle. Proximal motion of the shuttle may cause the tensile force exerted by the trip spring to be reduced. The trip sensor may be configured to transmit control signals to indicate the target tissue is clamped between the clamp and the piston assembly.

According to aspects, the piston assembly includes an inner piston, an outer piston, and a piston spring. The inner piston may be coupled to the first drive shaft. The outer piston may enclose at least a portion of the inner piston. The piston spring may be interposed between the inner piston and the outer piston. Rotation of the first drive shaft in a first direction may cause the inner piston to advance distally to compress the piston spring. Compression of the piston spring as the inner piston advances distally may cause the outer piston to advance distally and compress target tissue.

In aspects, the sensing device further includes a controller operatively coupled to the sensor. The controller may be configured to receive sensor signals from the sensor indicative of one or more tissue properties. In response, the sensing device may display a visual representation of the one or more tissue properties. The one or more tissue properties may include at least one tissue property selected from the group consisting of tissue temperature, tissue impedance, tissue permittivity, tissue permeability, tissue elasticity, and force applied to electrosurgical instrument.

According to aspects, a controller may be operatively coupled to the shuttle sensor, the trip sensor, a first motor operatively coupled to the first drive shaft and a second motor operatively coupled to the second drive shaft. The controller may be configured to receive sensor signals from the trip sensor, and transmit control signals to cause the first motor to remain at a first position in response to receiving the sensor signals from the trip sensor. The controller may be configured to receive sensor signals from an encoder disposed about the second drive shaft, calculate an amount of rotations for compressing target tissue, and transmit control signals to cause the second motor to rotate the second drive shaft a predetermined number of rotations to compress target tissue. Calculating the amount of rotations may further include receiving sensor signals from an encoder disposed about the first drive shaft. Calculating the amount of rotations may be based on the sensor signals received from the encoder disposed on the first drive shaft and the encoder disposed on the second drive shaft.

According to another example embodiment herein, a method for sensing a tissue property includes advancing a shuttle having a clamp proximally toward a piston assembly to compress target tissue against a sensor, advancing an outer piston assembly distally to compress target tissue, and transmitting sensor signals indicative of at least one tissue property to a controller.

In aspects, advancing the shuttle may include advancing the shuttle to a first position when a predetermined force is applied by the shuttle to target tissue. The method for sensing a tissue property may further include receiving sensor signals from a trip sensor indicating that a predetermined amount of force is exerted on target tissue, and stopping proximal advancement of the shuttle in response to receiving the sensor signals from the trip sensor while the predetermined amount of force is exerted on target tissue. Advancing the outer piston may include advancing the outer piston a first distance. The method may further include determining a position of the outer piston, and calculating a first distance based on the position of the outer piston. Advancing the outer piston the first distance may cause a predetermined compressive force to be applied to target tissue.

According to another example embodiment herein, a system for determining a tissue property includes a sensing device and a handheld device. The sensing device includes an adapter assembly, an actuation assembly, a shuttle, and a piston assembly. The adapter assembly is configured to couple to surgical handheld devices. The actuation assembly extends distally from the adapter assembly. The adapter assembly is configured to operably couple to and be engaged by handheld devices coupled to the adapter assembly. The actuation assembly includes a first drive shaft and a second drive shaft. The shuttle includes a clamp and a shuttle sensor. The shuttle is coupled to the first drive shaft via a coupling. The shuttle sensor is disposed on the clamp. The piston assembly is coupled to the second drive shaft and is configured to compress target tissue between the piston assembly and the clamp of the shuttle. The handheld device includes a housing, a first rotatable drive connector configured to operably couple to the first drive shaft and a second rotatable drive connector configured to operably couple to the second drive shaft.

In aspects, the handheld device further includes a controller configured to transmit control signals to advance the shuttle proximally to clamp on target tissue, transmit control signals to advance the piston assembly distally to compress the target tissue, receive sensor signals from the sensor of the shuttle indicative of a tissue property selected from the group consisting of tissue temperature, tissue impedance, tissue permittivity, tissue permeability, tissue elasticity, and force applied by the sensing device to target tissue, and transmit control signals to display a visual representation of the sensed tissue property. The controller may be configured to receive sensor signals from a trip sensor operatively coupled to the shuttle and the first drive shaft, determine that target tissue is compressed with a predetermined force based on the sensor signal received from the trip sensor, and transmit control signals to cause the shuttle to remain at a first position in response to determining that target tissue is compressed with a predetermined force. The controller may be configured to receive sensor signals from an encoder disposed about the second drive shaft, calculate a distance to advance the piston assembly distally to compress target tissue, and transmit control signals to cause the piston assembly to advance distally based on the calculated distance.

BRIEF DESCRIPTION OF THE DRAWINGS

The accompanying drawings, which are incorporated in and constitute a part of the specification, illustrate embodiments of the disclosure and together with a general description of the disclosure given above, and the detailed description of the embodiment(s) given below, serve to explain the principles of the present disclosure.

DETAILED DESCRIPTION

Figure 1:
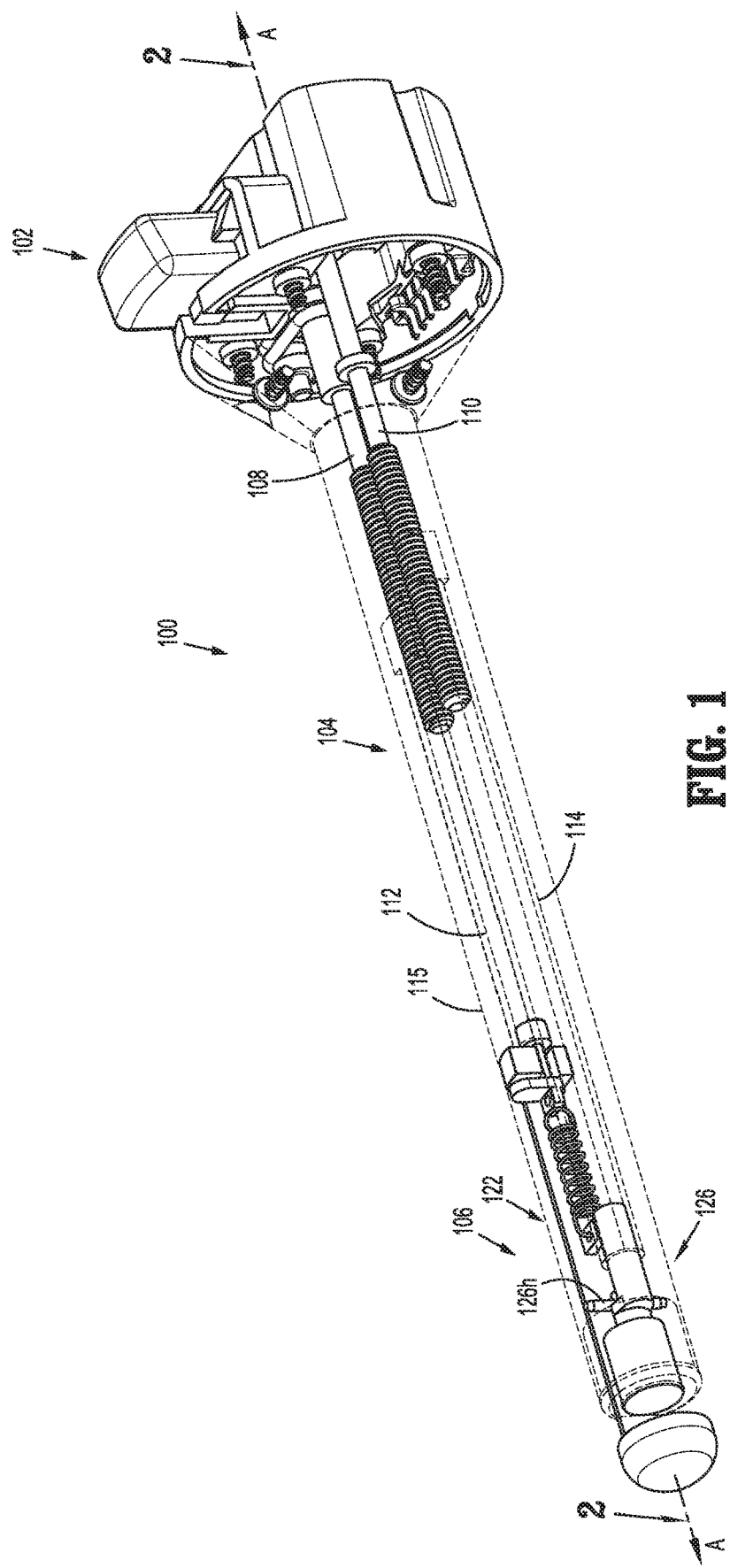
FIG. 1 is a perspective view of a tissue property sensing device provided in accordance with the present disclosure.

Embodiments of the presently described tissue sensing devices and methods are described in detail with reference to the drawings, in which like or corresponding reference numerals designate identical or corresponding elements in each of the several views.

Reference will now be made to terms used throughout the present disclosure to describe the principles of present disclosure. As used herein, the term "clinician" refers to a doctor, nurse, or other care providers and may include support personnel. As is traditional, the term "distal" refers to structure that is, in use, positioned farther from the clinician, whereas the term "proximal" refers to structure that is positioned closer to the clinician. Further, directional terms such as front, rear, upper, lower, top, bottom, distal, proximal, and the like are used to assist in understanding the description and are not intended to limit the present disclosure. The term "surgical field" refers to the space in which the surgical procedure is performed, and the term "surgical cavity" refers to a cavity at least partially surrounded by tissue.

Tissue property sensing devices (hereinafter "sensing devices") in accordance with illustrative embodiments of the present disclosure include an adapter assembly coupled to an outer cannula, an actuation assembly, and a sensing assembly. Tissue property sensing devices of the present disclosure are configured to be positioned about target tissue and compress the target tissue against one or more sensors. Compression of the target tissue enables measurement of tissue properties including, without limitation, tissue profusion, blood pressure, oxygen content of blood associated with the target tissue, tissue temperature, tissue impedance, tissue permittivity, tissue permeability, tissue elasticity, force applied by the sensing assembly to the target tissue, and the like.

In use, a clinician attaches the adapter assembly of the sensing device to a handheld device. The sensing device may be selectively engaged by the clinician operating the handheld device, with the handheld device being further configured to receive sensor signals from one or more sensors disposed about the sensing assembly. Additionally, the sensing device may be in wired or wireless electrical communication with a controller (hereinafter "electrical communication"). The controller may be disposed in the sensing device, the handheld device, or remotely. For a more detailed discussion on the construction and operation of handheld surgical devices, reference may be made to U.S. Patent Application Publication No. 2016/0310134, filed on Apr. 12, 2016, and entitled "HANDHELD ELECTROMECHANICAL SURGICAL SYSTEM", U.S. Patent Application Publication No. 2015/0157320, filed on Nov. 21, 2014, entitled "ADAPTER ASSEMBLY FOR INTERCONNECTING ELECTROMECHANICAL SURGICAL DEVICES AND SURGICAL LOADING UNITS, AND SURGICAL SYSTEMS THEREOF", and U.S. Patent Application Publication No. 2016/0310134, filed on Apr. 12, 2016, entitled "HANDHELD ELECTROMECHANICAL SURGICAL SYSTEM", the contents of each of which are herein incorporated by reference in their entirety.

After coupling the adapter assembly to the handheld device, the sensing device may be repositioned by the clinician within a body cavity of a patient. Specifically, the clinician may insert a distal portion of the sensing device into the body cavity of the patient and, subsequent to insertion, position the sensing device about target tissue to be acted upon. The sensing device may be mechanically engaged by the handheld device as a result of clinician engagement of the handheld device. Once the clinician engages the handheld device, one or more components of the actuation assembly, including a first drive screw and a second drive screw, are advanced distally. Specifically, a clamp and piston which are operably coupled to the handheld device via the actuation assembly may be advanced between proximal and distal positions to compress the target tissue therebetween.

Once a clinician identifies and positions the sensing assembly of the sensing device about target tissue for inspection, the clinician may engage the handheld device to cause one or more sensors disposed along the sensing assembly to measure one or more tissue properties of the target tissue. Additionally, or alternatively, the sensor may, during operation of the handheld device, continuously or intermittently transmit sensor signals in response to sensing one or more tissue properties. The sensed tissue properties may include, without limitation, tissue profusion, blood pressure, oxygen content of blood associated with the target tissue, tissue temperature, tissue impedance, tissue permittivity, tissue permeability, tissue elasticity, force applied by the sensing assembly to the target tissue, and the like.

Referring now to FIGS. 1-5, in accordance with the present disclosure, a sensing device 100 includes an adapter assembly 102, an actuation assembly 104 coupled to and extending distally from the adapter assembly 102, and a sensing assembly 106 coupled to a distal portion of actuation assembly 104. A distal portion of adapter assembly 102 is coupled to an outer cannula 115 which encloses at least a portion of actuation assembly 104 and sensing assembly 106. Adapter assembly 102 includes rotatable drive connectors sleeves (not shown) which extend proximally from adapter assembly 102, and which are configured to be mechanically mated with rotatable drive connectors 208 of a handheld device 200 (see FIG. 6).

The rotatable drive connector sleeves are coupled, in fixed axial alignment, to a first drive screw or first drive 108, and a second drive screw or second drive 110. First drive 108 and second drive 110 extend distally from adapter assembly 102 and may be independently rotated by corresponding drive connectors (e.g., rotatable drive connectors 208) of the handheld device 200 (see FIG. 6). A distal portion of first drive 108 and a distal portion of second drive 110 have a threaded surface 108a, 110a to facilitate rotational engagement of a first drive shaft 112 and a second drive shaft 114.

The first drive shaft 112 and the second drive shaft 114 have a first tubular member 112a and a second tubular member 114a, respectively, both of which retain cylindrical configurations. First tubular member 112a has an outer surface and an inner surface. Similarly, second tubular member 114a has an outer surface and an inner surface. The inner surfaces of both first tubular member 112a and second tubular member 114a have threaded recesses 112b, 114b disposed along proximal portions of the respective inner surface. Threaded recesses 112b, 114b are configured to receive and to be rotatably engaged by the distal portion of first drive 108 and second drive 110 of adapter assembly 102. As first drive 108 or second drive 110 rotate clockwise (from the perspective of the clinician), respective threaded surfaces 108a, 110a rotatably engage threaded recesses 112b, 114b, selectively advancing either first drive shaft 112 or second drive shaft 114 distally relative to adapter assembly 102. Alternatively, when first drive 108 or second drive 110 rotates counter-clockwise, first drive shaft 112 or second drive shafts 114 retract proximally relative to adapter assembly 102.

Figure 3A:
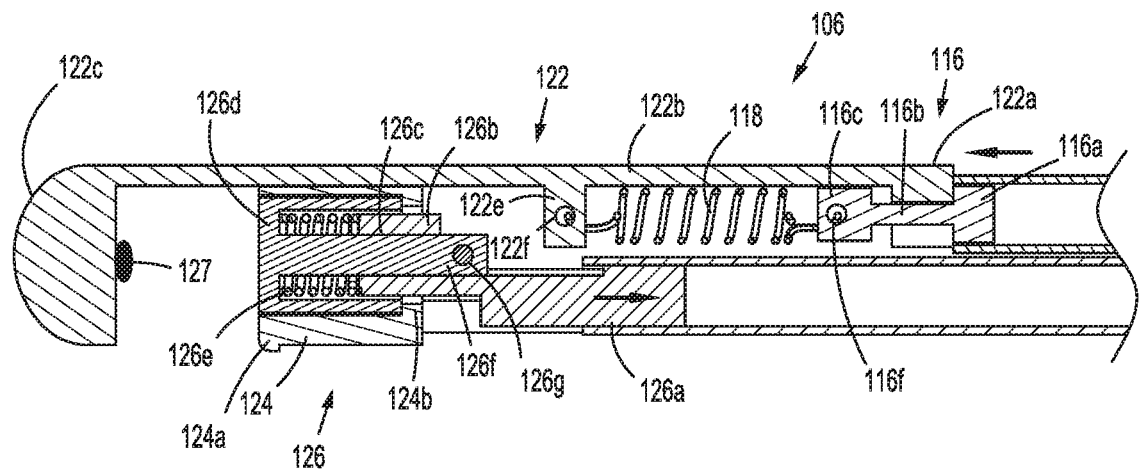
FIG. 3A is an enlarged view of a distal portion of the tissue property sensing device of FIG. 2 is shown in a first position.
Figure 3B:
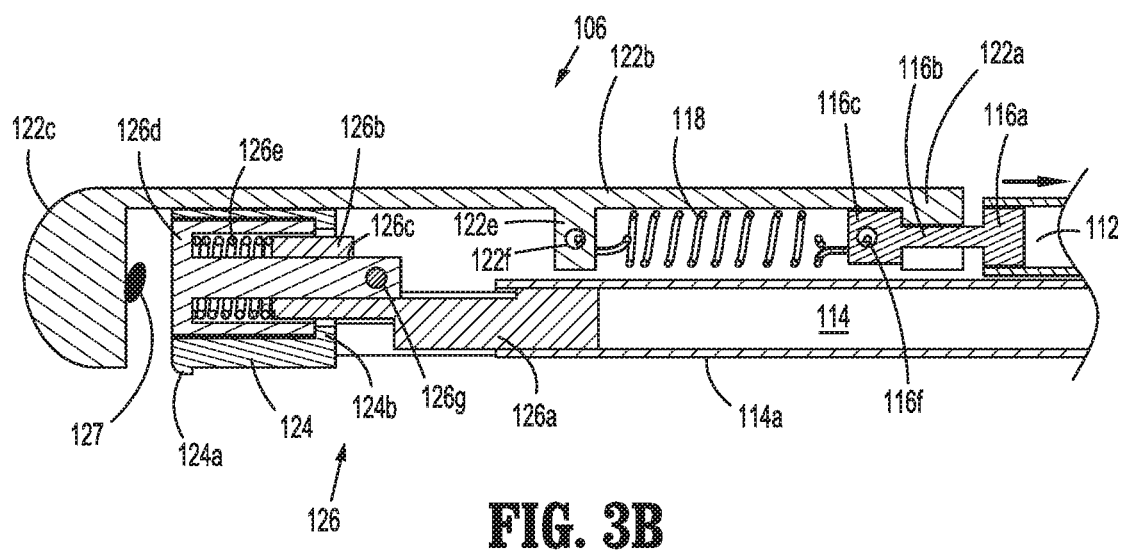
FIG. 3B is an enlarged view of a distal portion of the tissue property sensing device of FIG. 2 is shown in a second position.

Referring now to FIGS. 3A and 3B, the distal portion of first drive shaft 112 has a coupling 116 fixably coupled thereto. Coupling 116 includes a base 116a defining an exterior surface and a proximal surface. Base 116a is configured to be inserted in and coupled to the distal portion of first drive shaft 112. Specifically, the exterior surface of base 116a is configured to be inserted proximally in and fixed to the interior surface of first tubular member 112a. Base 116a of coupling 116 may be affixed to first drive shaft 112 via any suitable method such as, without limitation, via an adhesive, friction fit, etc. By virtue of coupling base 116a to first tubular member 112a, coupling 116 receives and transfers proximal and distal force between first drive shaft 112 and the sensing assembly 106.

Figure 2:
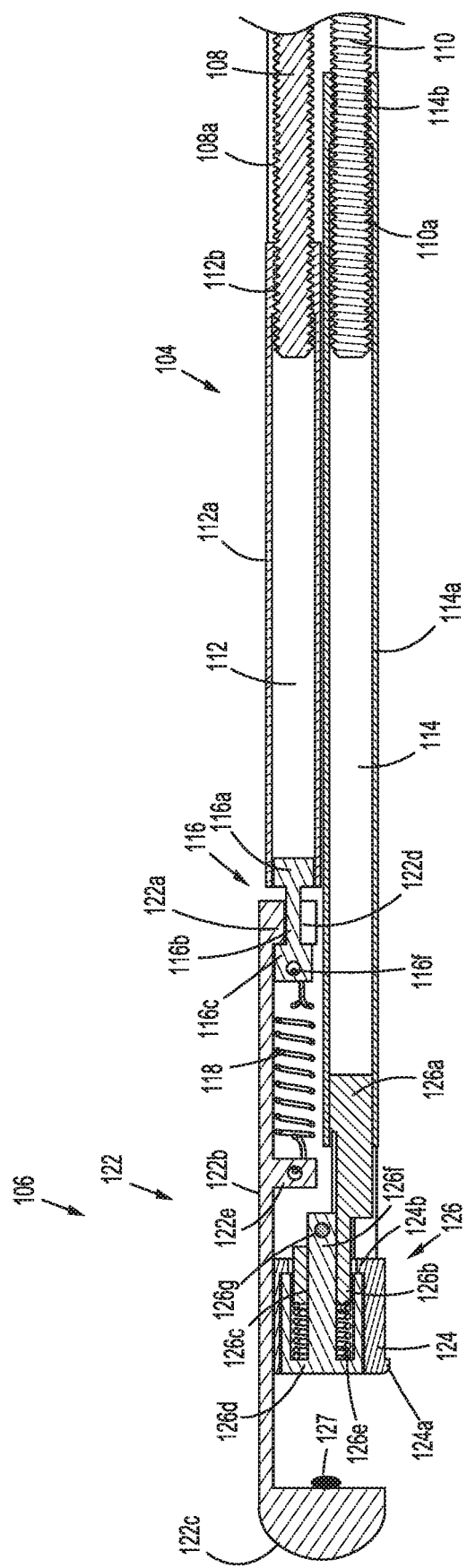
FIG. 2 is a transverse, cross-sectional view taken across section line 2-2 in FIG. 1.
Figure 4A:
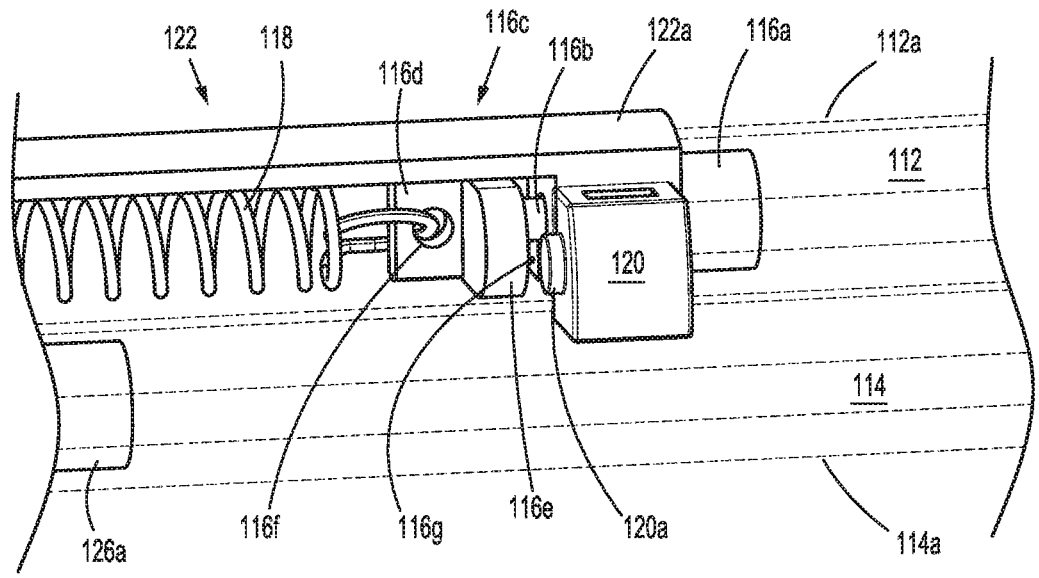
FIG. 4A is an enlarged perspective view of a force limiting switch illustrated relative to a coupling disposed within the tissue property sensing device of FIG. 1, shown in a first position.
Figure 4B:
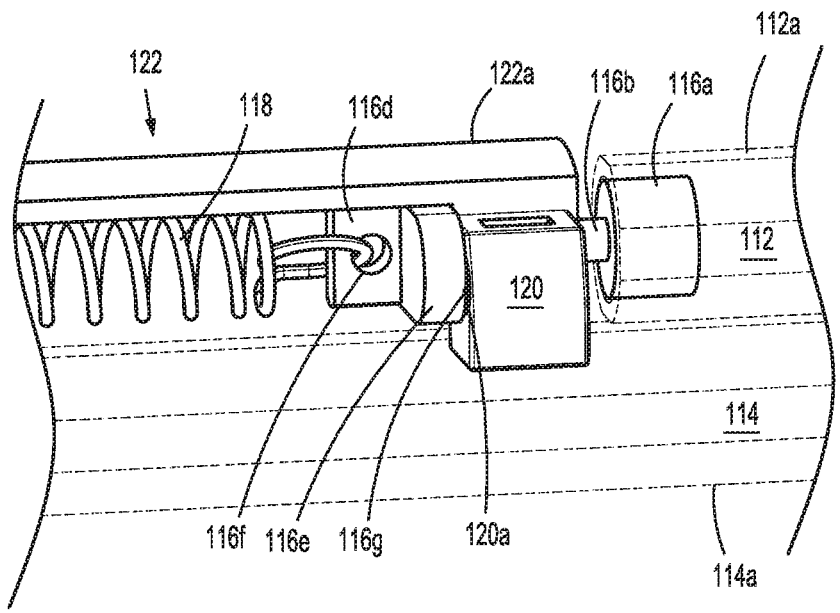
FIG. 4B is an enlarged perspective view of the force limiting switch illustrated relative to the coupling disposed within the tissue property sensing device of FIG. 1, shown in a second position.
Figure 5:
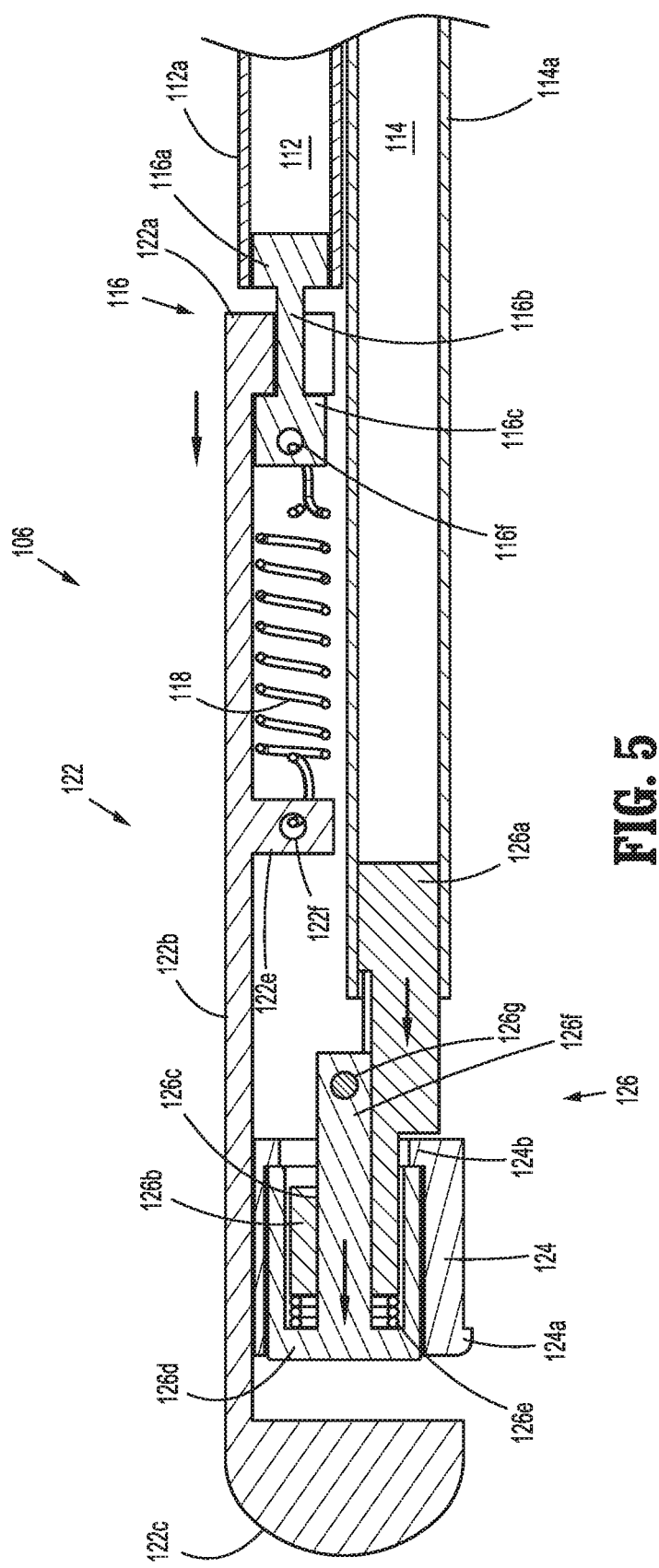
FIG. 5 is a transverse, cross-sectional view of the distal portion of the tissue property sensing device of FIG. 1 with a piston assembly advanced distally.

With reference to FIG. 2, base 116a of coupling 116 has a beam 116b extending distally therefrom. Beam 116b has a diameter less than a diameter of base 116a. Coupling 116 includes a head 116c distally coupled to beam 116b. Head 116c further includes a longitudinal flange 116d and a transverse flange 116e (FIGS. 4A-4B). Specifically, beam 116b couples to longitudinal flange 116d and is located proximal relative to transverse flange 116e which extends transverse relative to longitudinal flange 116d. Similar to base 116a, transverse flange 116e extends outward and has a diameter greater than that of beam 116b. As a result of this configuration, coupling 116 has a substantially "bar-bell" or "dog bone" shape or configuration when viewed from the side (e.g., as shown in FIGS. 2 and 3A-3B). It is contemplated that, while coupling 116 has a "bar-bell" shape, other shapes may be formed by coupling 116 without departing from the scope of the present disclosure.

Head 116c, and specifically longitudinal flange 116d of coupling 116, has a transverse bore 116f extending therethrough. Transverse bore 116f is located distal along longitudinal flange 116d relative to transverse flange 116e. Transverse bore 116f is configured to receive a proximal portion of a trip spring 118 therein, as well as to receive a distal force from trip spring 118. A proximal surface of transverse flange 116e further includes an electrical contact 116g disposed thereon. Electrical contact 116g of transverse flange 116e is configured and aligned to engage an electrical contact 120a of a trip sensor 120, when advanced proximally (see FIG. 4A).

Sensing device 100 further includes a shuttle 122 slidably coupled to coupling 116 and extending beyond a piston housing 124. Shuttle 122 has a shuttle base 122a and a shuttle arm 122b extending distally therefrom. Shuttle arm 122b couples distally to a clamp 122c. Shuttle base 122a defines a longitudinal opening 122d that is axially aligned with beam 116b of coupling 116 when coupled to sensing device 100. More particularly, shuttle base 122a includes an outer surface and an inner surface. The outer surface of shuttle base 122a further has trip sensor 120 disposed thereon. The inner surface of shuttle base 122a is configured to, when assembled, surround at least a portion of beam 116b, thereby maintaining the position of beam 116b relative to longitudinal opening 122d of shuttle base 122a during operation of sensing device 100.

Shuttle base 122a of the shuttle 122, and more specifically the longitudinal opening of shuttle base 122a, defines a longitudinal length "L1". In relation to coupling 116, the length "L1" of shuttle base 122a is less than a length "L2" formed by beam 116b of coupling 116. Length "L2" of beam 116b is defined as the length extending between base 116a and head 116c. In operation, beam 116b of coupling 116 may, as shuttle 122 is translated proximally or distally, traverse at least a portion of longitudinal opening 122d of shuttle base 122a. Due to the diameter of base 116a and head 116c of coupling 116 being greater than that of longitudinal opening 122d, shuttle base 122a is limited in motion relative to coupling 116, thereby limiting the movement of shuttle 122 as it traverses longitudinal axis A-A.

Shuttle arm 122b of shuttle 122 extends distally from shuttle base 122a, supportably coupling clamp 112c and shuttle base 122a. Shuttle arm 122b further has a transverse shuttle flange 122e extending therefrom. Transverse shuttle flange 122e extends in parallel relation to shuttle base 122a and defines a bore 122f therein. Bore 122f is configured to receivably couple a distal portion of trip spring 118 therein, as well as to receive proximal forces exerted by trip spring 118 during operation of sensing device 100. Additionally, when shuttle 122 is translated proximally, trip spring 118 contracts, thereby reducing the tensile force exerted by the trip spring 118 on the shuttle 122 and the coupling 116. Clamp 122c of shuttle 122 has a proximal-facing surface which includes at least one sensor 127 disposed thereon. Sensor 127, as noted above, is configured to sense one or more tissue properties including, without limitation, tissue profusion, blood pressure, oxygen content of blood associated with the target tissue, tissue temperature, tissue impedance, tissue permittivity, tissue permeability, tissue elasticity, force applied by the sensor assembly to the target tissue, and the like.

With continued reference to FIGS. 3A and 3B, the distal portion of second drive shaft 114 has a piston assembly 126 coupled thereto. Specifically, second drive shaft 114 couples to a piston column 126a having an inner piston head 126b extending from a distal portion of piston column 126a. Inner piston head 126b defines a bore 126c therein extending longitudinally therethrough. Similar to base 116a of coupling 116, the proximal portion of piston column 126a has an outer surface configured to be inserted and coupled to the distal portion of second drive shaft 114. The proximal portion of piston column 126a is configured to engage the interior surface of second tubular member 114a of second drive shaft 114. Piston column 126a may be affixed to second drive shaft 114 via any suitable method such as, without limitation, via an adhesive, friction fit, etc. By virtue of affixing the proximal portion of piston column 126a to second tubular member 114a, piston assembly 126, including inner piston head 126b and piston column 126a, may receive and transfer both proximal and distal forces from second drive shaft 114 to the target tissue.

Inner piston head 126b of piston assembly 126 couples to a distal portion of piston column 126a and has an outer surface defining a substantially cylindrical configuration. In use, inner piston head 126b is configured to be slidably received along an inner surface of outer piston head 126d. Inner piston head 126b also has a distal surface configured to receive and compress a piston spring 126e when advanced toward outer piston head 126d.

Outer piston head 126d of piston assembly 126 defines an inner surface and an outer surface. The inner surface of outer piston head 126d forms a cavity configured to slidably receive at least a portion of inner piston head 126b, as well as to receive piston spring 126e therebetween. More particularly, as second drive shaft 114 is advanced distally by second drive 110, inner piston head 126b of piston assembly 126 advances distally through the cavity formed by outer piston head 126d. As inner piston head 126b advances distally, it compresses piston spring 126e causing piston spring 126e to apply distal pressure to outer piston head 126d.

Outer piston head 126d of piston assembly 126 has a beam 126f extending proximally from the inner surface of outer piston head 126d. Beam 126f includes a transverse bore 126g located along a proximal portion thereof. A pin 126h (FIG. 1) is slidably received within transverse bore 126g and, when positioned therein, extends outward relative to a central axis extending longitudinally along a central portion of transverse bore 126g. As piston column 126a is advanced proximally, the proximal portion of inner piston head 126b contacts pin 126h, thereby causing outer piston head 126d to advance proximally. Transverse bore 126g of beam 126f is configured to receive a distal portion of a tension spring (not shown) as well as proximal forces received as a result of engagement of beam 126f by the tension spring. As a result, when the inner piston head 126b has not yet compressed piston spring 126e sufficiently to overcome force received by piston spring 126e, outer piston head 126d remains in a proximal-most position.

As shown in FIGS. 3A-3B, outer piston head 126d of piston assembly 126 is received within a piston housing 124 of sensing assembly 106. Piston housing 124 has an inner surface, an outer surface, and a distal flange 124a extending across and protruding from the distal portion of the outer surface. When assembled, piston housing 124 couples to the distal portion of an outer cannula 115 (see FIG. 1). Specifically, the outer surface of piston housing 124 is configured to be inserted proximally and fixed to the inner surface of outer cannula 115. Piston housing 124 may be affixed to outer cannula 115 via any suitable method such as, without limitation, via an adhesive, friction fit, etc. Distal flange 124a of piston housing 124 is configured to sit flush against the distal portion of outer cannula 115. Piston housing 124 further includes a proximal flange 124b extending inward. Proximal flange 124b is configured to limit proximal motion of outer piston head 126d relative to sensing device 100. In embodiments, when outer piston head 126d is in a proximal-most position (see FIG. 3A) the distal surface of outer piston head 126d aligns with distal flange 124a of piston housing 124. As a result of the mating of the distal surface of outer piston head 126d and distal flange 124a, a smooth surface is formed to prevent inadvertent engagement of tissue within the body cavity of the patient as sensing device 100 is positioned within the body cavity.

Figure 6:
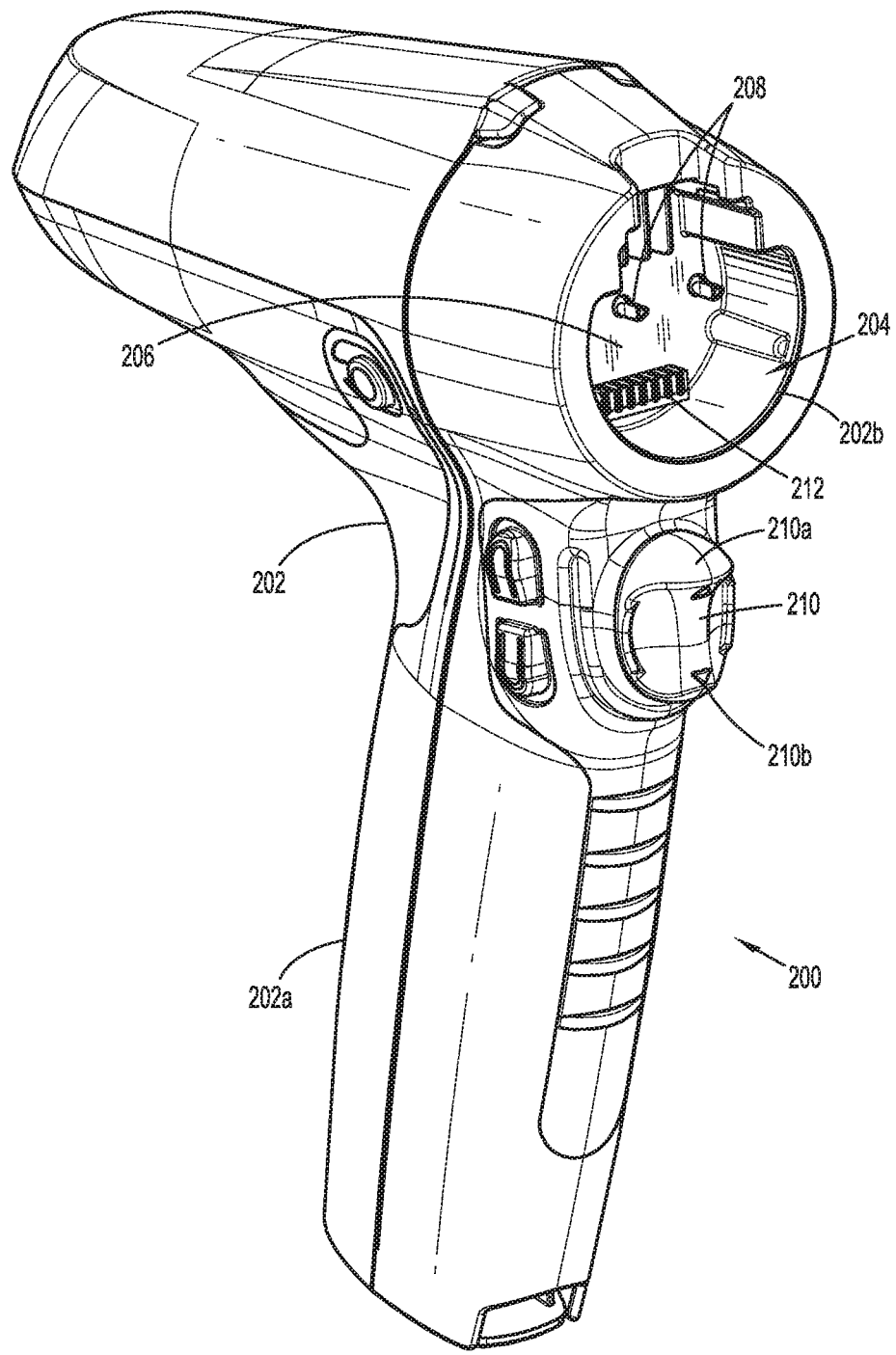
FIG. 6 is a perspective view of a handle assembly for connection with the tissue property sensing device of FIGS. 1-5, forming a surgical system.

Referring now to FIG. 6, a handheld device configured to connect to the sensing device 100 (FIG. 1) is shown, and designated generally 200. Handheld device 200 includes a housing 202 having a handle portion 202a, and a connecting portion 202b. The connecting portion 202b is configured to selectively couple to the adapter assembly 106. More specifically, the connecting portion 202b has a recess 204 which extends proximally inward to a proximal connecting surface 206. The connecting portion 202b of handheld device 200 further includes electrical contacts 212 extending distally from connecting surface 206 and configured to mate with electrical contacts (not shown) located on the adapter assembly 102. The connecting portion 202b of handheld device 200 further has rotatable drive connectors 208 configured to mate with rotatable drive connector sleeves (not shown) located on the adapter assembly 102. When coupled, electrical contacts 212 are operably coupled to and configured to transmit electrical signals to and from components of the sensing device 100 including the trip sensor 120, the one or more sensors 127 disposed on the shuttle 122, and the one or more encoders (not shown) operably coupled to the first drive shaft 112 and the second drive shaft 114.

Figure 7:
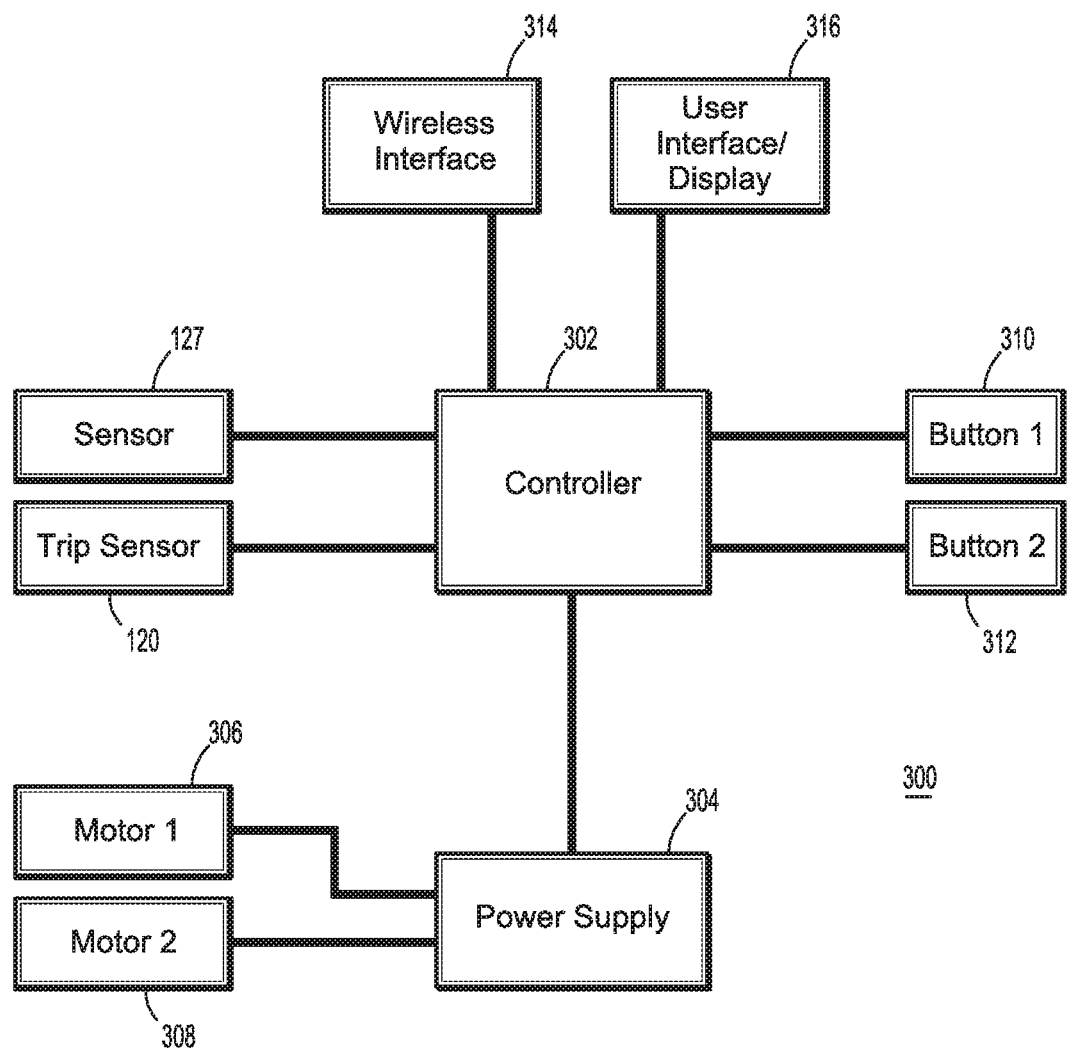
FIG. 7 is a schematic diagram of a control assembly in accordance with the present disclosure.

Referring now to FIG. 7, a schematic diagram of a control assembly is shown, and designated generally 200. Control assembly 300 includes a controller 302 which is disposed within handheld devices (e.g., handheld device 200) coupled to sensing device 100. The controller 302 is in electrical communication with, and receives electrical power from, a power supply 304. The controller 302 is configured to transmit control signals to the power supply 304 to selectively transmit power to a first motor 306 and a second motor 308. The controller 302 is also in electrical communication with the first motor 306 and the second motor 308 and transmits control signals thereto to cause a drive shaft extending from each respective motor to rotate clockwise or counter-clockwise.

A rocker 210 disposed on the handheld device 200 has a first button 210a and a second button 210b (see FIG. 6). When engaged by the clinician, the first button 210a and the second button 210b transmit sensor signals to the controller 302 to cause the controller 302 to activate the first motor 306 or the second motor 308. In response to user engagement of the first button 210a and the second button 21b, the controller 302 may transmit control signals to a user interface to indicate the status of the sensing assembly 100 as well as components incorporated in the control assembly 300. The controller 302 is further configured to receive sensor signals from trip sensor 120 (see FIG. 5) to indicate when a desired clamping force is exerted on the target tissue, as described above. Optionally, the controller 302 may receive wireless electrical communication with either trip sensor 120 or sensor 127. Specifically, controller 302 may be coupled to a wireless interface 314 configured to wirelessly communicate with sensor 127 and/or trip sensor 120 via any suitable wireless communication protocol (e.g., Wi-Fi, Bluetooth, LTE). While the target tissue of the patient is compressed against sensor 127, sensor 127 is configured to transmit sensor signals to the controller indicative of the one or more sensed tissue properties.

Referring again to FIGS. 1-5, encoders (not shown) may be disposed about first drive shaft 112 and second drive shaft 114. The encoders may be in electrical communication with the controller 302 and configured to transmit sensor signals indicative of the rotational or longitudinal position of first drive shaft 112 and second drive shaft 114 when urged between proximal and distal positions. Similarly, encoders may be disposed about first drive 108 and second drive 110 and similarly may transmit sensor signals indicative of the rotational or longitudinal position of first drive 108 and second drive 110. Discussion of the calculation of compressive force based on measurement of the rotation of the first or second drive 110, 112, or any corresponding components which are acted upon as the first or second drive 110, 112 will be provided in detail.

In response to receiving sensor signals from the encoders (not shown) coupled to first drive shaft 112, second drive shaft 114, first drive 108, and/or second drive 110, controller 302 may calculate the pressure applied or exerted on target tissue located between clamp 122c and piston assembly 126 as the target tissue is compressed therebetween. (See FIG. 8.) Notably, since the compressive force of trip spring 118 and piston spring 126e does not vary when the ambient air pressure, in which tissue property sensing device 100 is being operated in, is increased or decreased, controller 302 may accurately determine the pressure applied to target tissue as the tissue is compressed.

During surgical procedures, shuttle 122 is translated between distal positions (see FIG. 3A) and proximal positions (see FIG. 3B) when the clinician causes first drive 108 to be engaged. Similarly, piston assembly 126, including inner piston head 126b and outer piston head 126d, is translated between proximal positions (see FIG. 2) and distal positions (see FIG. 5) when the clinician causes second drive 110 to be engaged. Generally, in use, once the clinician inserts and positions the distal portion of sensing device 100 relative to the target tissue, the clinician may selectively engage sensing device 100. Specifically, the clinician may adjust the position of shuttle 122 and piston assembly 126 relative to sensing device 100 to enable measurement of one or more tissue properties of the target tissue via sensor 127 disposed on shuttle 122.

Initially, in operation, piston assembly 126 is positioned in a proximal-most position (see FIG. 3A) prior to insertion into the body cavity of the patient. The clinician may advance shuttle 122 to a desired position between and/or including the proximal-most or distal-most position relative to sensing device 100. Once the distal portion of sensing device 100 is positioned proximate to the target tissue, the clinician advances shuttle 122 distally to facilitate positioning the target tissue between clamp 122c and piston assembly 126. After the target tissue is positioned as desired between clamp 122c and piston assembly 126, the clinician may engage the handheld device 200 to cause the handheld device 200 to rotate first drive 108 counter-clockwise. In response, first drive shaft 112, which is operably coupled to shuttle 122, is advanced proximally, thereby advancing shuttle 122 and compressing the target tissue between piston assembly 126 and shuttle 122.

As the target tissue is compressed, the target tissue resists the compression, and applies an opposing force to clamp 122c. Once the opposing force is great enough to overcome a force exerted by trip spring 118, first drive shaft 112 continues to rotate, thereby drawing coupling 116 proximally relative to shuttle base 122a. Once electrical contact 116g, disposed on coupling 116, engages electrical contact 120a, a sensor signal is sent by trip sensor 120 to controller 302 indicating that a desired clamping force is exerted by sensing assembly 106 on the target tissue. The desired clamping force is predetermined, though may vary, and is based on the configuration (e.g., spring constant) of trip spring 118.

Once clamp 122c of shuttle 122 engages the target tissue, and causes trip sensor 120 to transmit sensor signals to controller 302 to indicate successful clamping of the target tissue, handheld device 200 may audibly or visually indicate to the clinician that the target tissue is ready to be compressed by piston assembly 126. Such audible or visual indication may include, without limitation, an audible sound or tone, indication via one or more light sources projecting light from handheld device 200, etc.

Upon indication that the target tissue has been successfully clamped, the clinician engages handheld device 200 to cause second drive 110 to be rotated by handheld device 200. Specifically, handheld device 200 causes second drive 110 to rotate clockwise, advancing second drive shaft 114 distally. As second drive shaft 114 is advanced distally, inner piston head 126b, which is operably coupled to second drive shaft 114, compresses piston spring 126e in the cavity defined by outer piston head 126d. As inner piston head 126b compresses piston spring 126e, the force applied by inner piston head 126b overcomes the competing force received by outer piston head 126d from the tension spring (not shown). Outer piston head 126d is subsequently urged distally, thereby further compressing the target tissue.

Continued compression of the target tissue enables sensor 127 to measure one or more tissue properties. As sensor 127 measures the tissue properties, sensor signals are transmitted to controller 302 indicative of the sensed measurements. The sensor signals are subsequently interpreted by controller 302 and communicated to the clinician. Communication of the sensor signal data may include, without limitation, displaying visual representations of the sensed tissue properties on a display, either located on the handheld device or remotely.

To release the target tissue from sensing assembly 106, the clinician may again engage the handheld device to cause first drive 108 and second drive 110 to engage shuttle 122 and piston assembly 126, respectively. As the distance between the clamp 122c and the piston assembly 126 increases, the compressive force exerted on the tissue is reduced, thereby permitting the target tissue to move freely relative to the sensing device. After adjusting the placement of the target tissue relative to the sensing device 100, the clinician removes the distal portion of sensing device 100.

Figure 8:
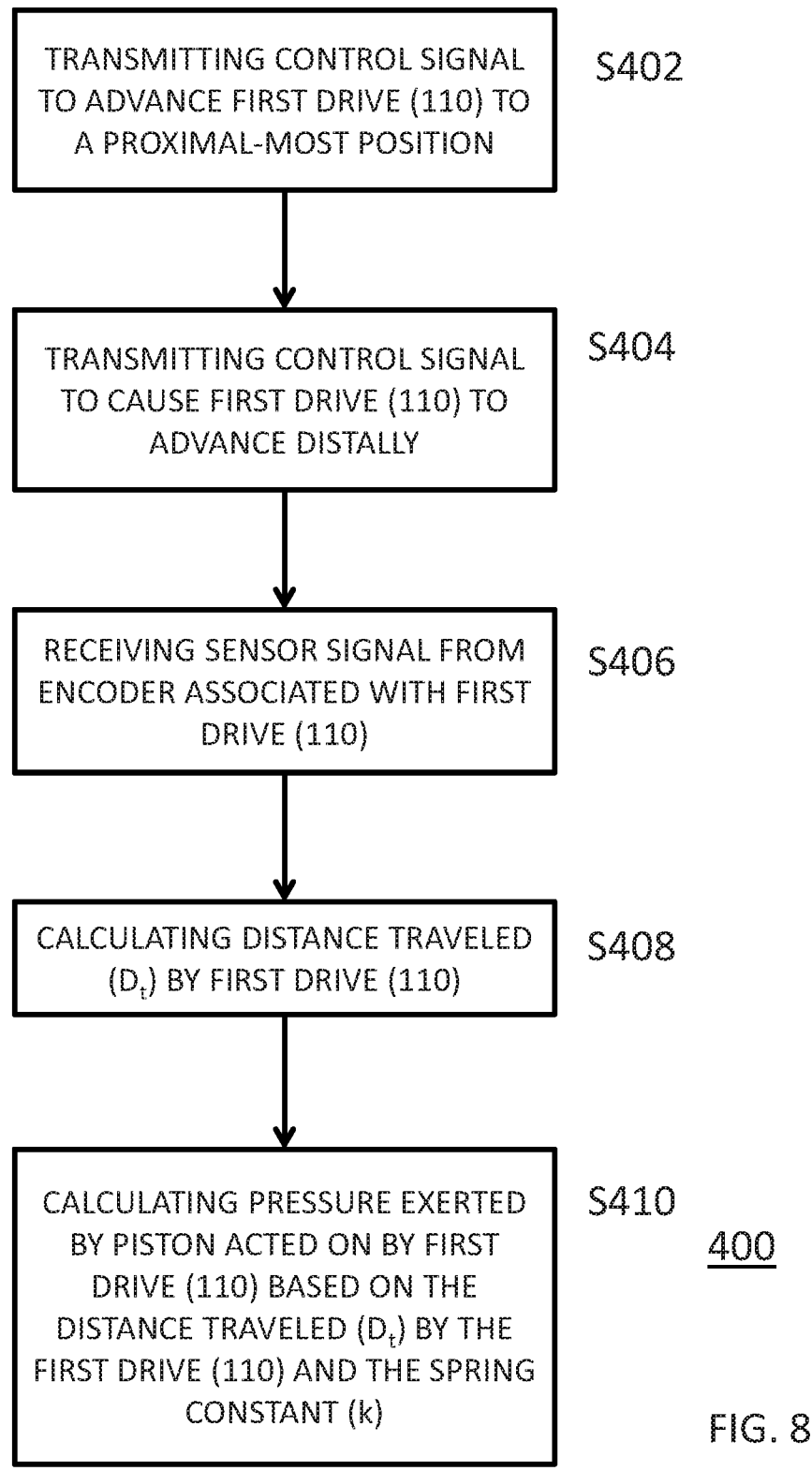
FIG. 8 is a flow diagram of a method of calculating compressive force exerted on target tissue by the tissue property sensing device of FIG. 1.

Referring now to FIG. 8, illustrated is a method or process of calculating a compressive force exerted on target tissue by the tissue property sensing device 100, generally referred to as process 400. While operating the tissue property sensing device 100, one or more compressive force measurements may be calculated based on the distance traveled longitudinally by the first or second drive 110, 112, and by extension the first or second drive shaft 114, 116. For purposes of clarity, calculation of the compressive force exerted by tissue property sensing device 100 will be discussed in detail with respect to motion of first drive 110 and first drive shaft 114 relative to piston spring 126e, however, it should be noted that compressive force exerted by proximal or distal motion of various components of tissue property sensing device 100 may be calculated in a similar fashion.

To calculate the compressive force exerted on target tissue by the tissue property sensing device 100 during operation, inner piston 126 may be initially retracted to a proximal-most position relative to the tissue property sensing device 100 (S402). Once in the proximal-most position, the controller 302 transmits control signals to cause the second drive to rotate (S404), as the second drive 110 is rotated, thereby causing the second drive shaft 114 to advance distally along longitudinal axis A-A. The rotations of the second drive 110 are measured by one or more encoders associated with the second drive 110. Upon measurement, controller 302 receives sensor signals from the encoder or encoders associated with the second drive 110 (S406). The measurements of the rotation of the second drive 110 are subsequently analyzed by the controller 302 to determine travel of the second drive shaft 114 (S408). More particularly, since rotation of the second drive 110 is directly proportional to longitudinal movement of second drive shaft 114, the controller 302 calculates the distance traveled, either proximally or distally, by second drive shaft 114 as a function of the measured rotation of the second drive 110.

The distance traveled is calculated by multiplying the distance measured by the one or more encoders by a scaling factor "Sr", as shown below (S408).

$$D_t = E_1 \times S_f$$

where "$D_t$" corresponds to the resulting distance traveled by the second drive shaft 114, "$E_1$" corresponds to the distance measured by the one or more encoders associated with the second drive 110, and "$S_f$" corresponds to the scaling factor "$S_f$" which represents a value that, when multiplied with the encoder signal, accurately represents the distance traveled by the second drive shaft 114. Once the distance traveled "$D_t$" is calculated, the controller 302 multiplies the distance traveled "$D_t$" by a spring constant k associated with the spring, as shown below, to determine the applied force exerted by piston spring 126e.

$$F = k \times D_t$$

where "F" corresponds to the force exerted by piston spring 126e, "k" corresponds to the spring constant of piston spring 126e, and "$D_t$" corresponds to the distance by which piston spring 126e is compressed (e.g., the distance traveled by second drive shaft 114 second drive 110 advances distally). Once the force "F" exerted by piston spring 126e is calculated, controller 302 divides force "F" by the surface area of outer piston head 126d, to determine to the pressure exerted by outer piston head 126d onto target tissue disposed between outer piston head 126d and (S410).

It will be understood that various modifications may be made to the embodiments of the presently disclosed sensing device. Therefore, the above description should not be construed as limiting, but merely as exemplifications of embodiments. Those skilled in the art will envision other modifications within the scope and the spirit of the present disclosure.

What is claimed is:

1. A sensing device for sensing one or more tissue properties, the sensing device comprising:
   an adapter assembly configured to couple to surgical handheld devices;

an actuation assembly extending distally from the adapter assembly and configured to operably couple to and be engaged by the surgical handheld devices coupled to the adapter assembly, the actuation assembly comprising:
an outer cannula;
a first drive shaft extending through the outer cannula; and
a second drive shaft extending through the outer cannula and being adjacent to the first drive shaft;
a shuttle having a clamp and a shuttle sensor, the shuttle coupled to a distal end of the first drive shaft via a coupling and having the shuttle sensor disposed on the clamp, wherein actuation of the first drive shaft results in axial translation of the shuttle; and
a piston assembly coupled to a distal end of the second drive shaft, at a location proximal of the shuttle, wherein upon actuation of the second drive shaft, the piston assembly is axially translated to compress target tissue between the piston assembly and the clamp of the shuttle.

2. The sensing device of claim 1, wherein the shuttle sensor is configured to sense the one or more tissue properties selected from the group consisting of tissue temperature, tissue impedance, tissue permittivity, tissue permeability, tissue elasticity, and force applied by the sensing device to target tissue.

3. The sensing device of claim 1, wherein the first drive shaft and the second drive shaft of the actuation assembly are rotatably supported and configured to receive rotational force from motors operably coupled to the first drive shaft and the second drive shaft.

4. The sensing device of claim 3, wherein rotation of the first drive shaft in a first direction causes the shuttle to advance proximally to clamp the target tissue.

5. The sensing device of claim 4, wherein rotation of the second drive shaft in a first direction causes the piston assembly to advance distally to compress the target tissue.

6. The sensing device of claim 5, further comprising:
a trip sensor; and
a trip spring coupled to the coupling and the shuttle,
wherein the trip spring exerts a tensile force to urge the coupling toward a proximal-most position relative to the shuttle.

7. The sensing device of claim 6, wherein proximal motion of the shuttle causes the tensile force exerted by the trip spring to be reduced.

8. The sensing device of claim 7, wherein the trip sensor is configured to transmit control signals to indicate the target tissue is clamped between the clamp and the piston assembly.

9. The sensing device of claim 6, further comprising a controller operatively coupled to the shuttle sensor, the trip sensor, a first motor operatively coupled to the first drive shaft, and a second motor operatively coupled to the second drive shaft, the controller configured to:
receive sensor signals from the trip sensor; and
transmit control signals to cause the first motor to remain at a first position in response to receiving the sensor signals from the trip sensor.

10. The sensing device of claim 9, wherein the controller is further configured to:
receive sensor signals from an encoder disposed about the second drive shaft;
calculate an amount of rotations for compressing the target tissue; and
transmit control signals to cause the second motor to rotate the second drive shaft a predetermined number of rotations to compress the target tissue.

11. The sensing device of claim 10, wherein the calculation of the amount of rotations further includes receiving sensor signals from an encoder disposed about the first drive shaft.

12. The sensing device of claim 11, wherein the calculation of the amount of rotations is based on the sensor signals received from the encoder disposed about the first drive shaft and an encoder disposed about the second drive shaft.

13. The sensing device of claim 1, wherein the piston assembly comprises:
an inner piston coupled to the first drive shaft;
an outer piston enclosing at least a portion of the inner piston; and
a piston spring interposed between the inner piston and the outer piston.

14. The sensing device of claim 13, wherein rotation of the first drive shaft in a first direction causes the inner piston to advance distally to compress the piston spring.

15. The sensing device of claim 14, wherein compression of the piston spring as the inner piston advances distally causes the outer piston to advance distally and compress the target tissue.

16. The sensing device of claim 1, further comprising a controller operatively coupled to the shuttle sensor, the controller configured to receive sensor signals from the shuttle sensor indicative of the one or more tissue properties and, in response to receiving the shuttle sensor signals, display a visual representation of the one or more tissue properties.

17. The sensing device of claim 16, wherein the one or more tissue properties includes at least one tissue property selected from the group consisting of tissue temperature, tissue impedance, tissue permittivity, tissue permeability, tissue elasticity, and force applied to electrosurgical instrument.

18. A method of sensing at least one tissue property, the method comprising:
advancing a shuttle having a clamp proximally toward a piston assembly to compress a target tissue against a sensor;
advancing an outer piston of the piston assembly distally to compress the target tissue;
transmitting sensor signals indicative of the at least one tissue property to a controller;
determining a position of the outer piston;
calculating a first distance based on the position of the outer piston;
receiving sensor signals from a trip sensor indicating that a predetermined amount of force is exerted on the target tissue; and
stopping proximal advancement of the shuttle in response to receiving the sensor signals from the trip sensor while the predetermined amount of force is exerted on target tissue.

19. The method of claim 18, wherein advancing the shuttle includes advancing the shuttle to a first position when the predetermined amount of force is applied by the shuttle to the target tissue.

20. A system for determining a tissue property, the system comprising:
a sensing device comprising:
an adapter assembly configured to couple to surgical handheld devices;

an actuation assembly extending distally from the adapter assembly and configured to operably couple to and be engaged by the surgical handheld devices coupled to the adapter assembly, the actuation assembly comprising:
   a first drive shaft; and
   a second drive shaft;
a shuttle having a clamp and a shuttle sensor, the shuttle coupled to the first drive shaft via a coupling and having the shuttle sensor disposed on the clamp; and
a piston assembly coupled to the second drive shaft and configured to compress target tissue between the piston assembly and the clamp of the shuttle; and
a surgical handheld device comprising:
   a housing;
   a first rotatable drive connector configured to operably couple to the first drive shaft;
   a second rotatable drive connector configured to operably couple to the second drive shaft; and
   a controller configured to:
      transmit control signals to advance the shuttle proximally to clamp on the target tissue;
      transmit control signals to advance the piston assembly distally to compress the target tissue;
      receive sensor signals from the shuttle sensor indicative of the tissue property selected from the group consisting of tissue temperature, tissue impedance, tissue permittivity, tissue permeability, tissue elasticity, and force applied by the sensing device to the target tissue;
      transmit control signals to display a visual representation of the sensed tissue property;
      receive sensor signals from a trip sensor operatively coupled to the shuttle and the first drive shaft;
      determine that the target tissue is compressed with a predetermined force based on the sensor signal received from the trip sensor;
      transmit control signals to cause the shuttle to remain at a first position in response to determining that the target tissue is compressed with the predetermined force;
      receive sensor signals from an encoder disposed about the second drive shaft:
      calculate a distance to advance the piston assembly distally to compress the target tissue; and
      transmit control signals to cause the piston assembly to advance distally based on the calculated distance.

* * * * *